United States Patent [19]

Nelson

[11] 3,957,580

[45] May 18, 1976

[54] IMMOBILIZED MICROBIAL CELLS

[75] Inventor: Roger P. Nelson, Waterford, Conn.

[73] Assignee: Pfizer Inc., New York, N.Y.

[22] Filed: Mar. 27, 1974

[21] Appl. No.: 455,143

[52] U.S. Cl. .............................. 195/59; 195/31 F; 195/63; 195/68; 195/DIG. 11; 195/75
[51] Int. Cl.² ...................... C12K 1/00; C07G 7/02
[58] Field of Search .................. 195/31 R, 31 F, 59, 195/63, 68, DIG. 11

[56] References Cited
UNITED STATES PATENTS

| | | | |
|---|---|---|---|
| 3,282,702 | 11/1966 | Schreiner | 195/63 X |
| 3,779,869 | 12/1973 | Zienty | 195/68 |
| 3,791,926 | 2/1974 | Chibata et al. | 195/59 X |
| 3,806,417 | 4/1974 | Beaucamp et al. | 195/63 |
| 3,841,970 | 10/1974 | Matthews | 195/68 X |

OTHER PUBLICATIONS

Brown, A. D., The Development of Halophilic Properties in Bacterial Membranes by Acylation, Biochimica et Biophysica Acta. Vol. 93, 1964 (pp. 136–142).

*Primary Examiner*—David M. Naff
*Attorney, Agent, or Firm*—Connolly and Hutz

[57] ABSTRACT

Immobilized microbial cells are prepared by treating microbial cells with a polyfunctional cross-linking reagent and contacting the treated cells in aqueous medium with a water insoluble particulate polymer prepared by polymerizing an ethylenically unsaturated monomer. Alternatively, the treated cells may be bonded to the monomer prior to polymerizing.

18 Claims, No Drawings

IMMOBILIZED MICROBIAL CELLS

BACKGROUND OF THE INVENTION

This invention relates to polymeric enzyme products. More specifically, it relates to novel immobilied microbial cells and their preparation.

Enzymes, with their high degree of specificity, are far superior to conventional catalysts in many chemical reactions. Until recently, however, such factors as the high cost of isolation, the tendency toward instability when removed from the environment of the whole cell, and the availability only in soluble form, had severely limited enzyme use.

The immobilization of enzymes by attachment to, or entrapment within, solid support material has helped to overcome some of these difficulties and to make enzyme use more economical. The various physical and chemical methods employed for the immobilization are discussed in such reviews as *Immobilized Enzymes* by O. R. Zaborsky (CRC Press, 1973).

Immobilization of the whole cell itself to overcome enzyme isolation and stability problems has also been employed. Its use to date, however, has been limited to physical methods of immobilization. Typical examples are the adsorption of cells of Streptomyces phaeochromogenes containing active glucose isomerase on reconstituted hide collagen (Biotech. & Bioengr., XV, p. 565 (1973), and the gel entrapment of fungal cells containing hydroxylase enzyme for the conversion of Compound S to cortisol (Scientific American, Mar. 1971, p. 30). These immobilization methods do not, however, preclude disassociation of the cells from the support medium. The nature of the binding forces is such that reaction conditions may be severely limited in order to prevent or minimize such disassociation with attendant loss of enzymatic activity and possible contamination of the process stream. A more stable cell immobilization system is therefore the object of this invention.

SUMMARY OF THE INVENTION

It has now been found that microbial cells can be effectively immobilized by chemical covalent bonding of the cells to water-insoluble particulate polymer matrix. The chemical bond can be formed either with the preformed polymer or with reactive monomer prior to polymerization. Further, treatment of the cells with a polyfunctional cross-linking agent either prior to, during or after bonding reduces enzyme loss from the cell.

DETAILED DESCRIPTION OF THE INVENTION

In the practice of this invention, intact microbial cells are chemically bonded to water-insoluble particulate polymer through reactive groups on the polymer. While chemical covalent bonding of isolated enzymes to polymer is currently common practice, the discovery that whole cells themselves, which are the source of and orders of magnitude larger than enzymes, can also be effectively immobilized by chemical covalent bonding is indeed surprising. Such bonding will frequently occur by reaction of cell amino groups with the reactive polymer substituents. In addition, other groups such as hydroxyl and sulfhydryl are also available in the cells and can play a role in the bonding mechanism. This is true because amino-reacting polymer substituents, for example epoxide, halo carbonyl and halomethyl carbonyl groups, are also reactive toward hydroxyl and sulfhydryl groups such as are present in the cells.

The bondng can occur either before or after the polymer formation. In the former case, the cells are contacted with a polymerizable ethylenically unsaturated monomer containing a reactive group, and the cell-carrying monomer is then polymerized or copolymerized in the presence of a cross-linking monomer and an initiator system. In the latter case, the cells are contacted directly with any particulate polymer containing a reactive group. This includes natural as well as synthetic organic polymers.

Polymerizable ethylenically unsaturated monomers and polymers derived therefrom suitable for practice of the present invention by either the pre- or post-bonding technique, respectively, include those having the formula I:

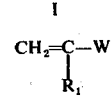

wherein
$R_1$ = hydrogen, methyl or chloro,
and

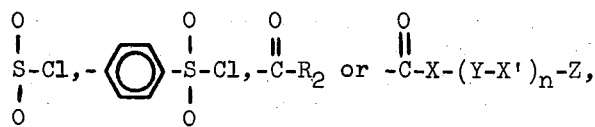

and wherein
$R_2$ = halo, azido, 2,3-epoxypropoxy, 2,3-epithiopropoxy, N-(2,3-epoxypropyl)amino, N-[(p-diazonium chloride)phenyl]amino, acryloyloxy, lower alkoxy carbonyloxy, or benzenesulfonyloxy,
X = oxygen or $NR_3$ where $R_3$ is hydrogen or alkyl of from 1 to 6 carbons,
Y = alkylene containing 2 or 3 carbons,
n = an integer of from 1 to 2,
Z = haloacetyl, 2-(4,6-dichloro)-s-triazinyl, p-toluenesulfonyl, p-(halomethyl)benzoyl, or cyano,
and
X' = X with the proviso that when Z is p-toluenesulfonyl, X' is oxygen.

Monomers and polymers containing epoxide, halocarbonyl and halomethyl carbonyl groups are preferred for the bonding. Especially desired are those polymers containing the reactive monomers 2,3-epoxypropyl methacrylate (glycidyl methacrylate), 2,3-epithiopropyl methacrylate, methacryloyl chloride and bromoacetylhydroxyethyl methacrylate.

In the case of monomers and polymers containing nonreactive functional groups, as when $R_2$ is hydroxy or Z is hydrogen in the above monomer formula I, the functional groups may be converted to reactive substituents by methods well known in the art. This often requires the use of multi-functional low molecular weight reagent. Thus, when $R_2$ is hydroxy in the formula I, the carboxyl groups of the monomer or polymer may be activated by reaction with an appropriate carboxylic group-activating reagent such as: a carbodiimide, for example, dicyclohexylcarbodiimide or ethylmorpholinocarbodiimide; N-ethyl-5-phenylisoxazolium-3′-sulfonate (Woodward's Reagent K); ketenimines such as pentamethyleneketene cyclohexylimine; acetylenic ethers, for example, ethoxyacetylene; hexahalocyclotriphosphatriazines; N-hydroxyphthalimide or N-hydroxysuccinimide and other reagents used to form a peptide bond. When Z is hydroen in the formula I, the monomer or polymer hydroxyl groups may likewise be activated by standard procedures with halo-Z, especially bromoacetyl bromide, cyanogen bromide and 2-amino-4,6-dichloro-1,3,5-triazine.

The immobilization process is applicable to all microbial cells such as bacteria, yeasts, actinomyces and fungi. Preferred cells are those in which the primary enzyme systems are oxidoreductases, especially those such as glucose oxidase which do not require soluble cofactors; hydrolases such as $\alpha,\beta$-amylases and peptidases, and especially penicillin acylase; lyases, preferably those concerned with breakage of carbon-oxygen bonds and especially those such as phenylalanine ammonia-lyase and aspartate ammonia-lyase which are concerned with breakage of carbon-nitrogen bonds; and isomerases such as racemases, epimerases, cis-trans isomerases, and especially glucose isomerase. Preferred bacterial genera include: Pseudomonas, Xanthomonas, Acetobacter, Alcaligenes, Flavobacterium, Escherichia, Aerobacter, Erwinia, Serratia, Proteus, Micrococcus, Sarcina, Lactobacillus, Bacillus, Nocardia, Streptomyces, and Corynebacterium. Preferred fungal and yeast genera include: Rhodotorula, Rhodosporidium, Sporobolomyces, Mucor, Fusarium, Penicillium, Aspergillus, Glomerella, Rhizopus, Saccharomyces, Conidiobolus, Byssochlamys, Candida, Chaetomium, Trichoderma, Septoria, Coprinus, Neurospora, Humucola, and Trichosporon. Preferred actinomyces genus is Micropolyspora. Especially preferred species are: *Escherichia coli, Bacterium cadaveris, Proteus rettgeri, Rhodotorula gracilis, Penicillium chrysogenum,* and *Aspergillus niger*.

The covalent bonding of the cells to reactive polymer, or the bonding to reactive monomer followed by monomer polymerization or copolymerization, is run in aqueous medium. While the temperature for bonding to polymer or monomer, or for polymerization after bonding to monomer, can vary over a wide range, the preferred range is from about 5° to 50°C, and especially from about 10° to 30°C. The time required for bonding will depend on the system and bonding temperature, but will normally be from about 0.5 to 35 hours; the preferred time for bonding to polymer is about 15 to 30 hours, while that for bonding to monomer is about 1 to 5 hours. Polymerizations are normally completed in about 1 to 6 hours. The weight ratio of polymer to cells (dry basis) can vary considerably, with the preferred ratio being from about 0.1 to 25 and especially from about 0.5 to 4.

When cells are bonded to reactive monomer, the subsequent aqueous addition polymerization is run, with or without one or more comonomers, in the presence of difunctional cross-linking monomer and an initiator system. Any of those comonomers, cross-linking monomers and initiator systems commonly used in this type of polymerization and which do not destroy the cell enzymatic activity can therefore readily be used.

Suitable comonomers are, for example, acrylic, α-chloroacrylic, methacrylic acids and the glycidyl, lower alkyl ester, N,N-(disubstituted)aminoalkyl esters, amides, lower alkyl substituted amides, methylol substituted amides, N-monosubstituted aminoalkylamides and N,N-disubstituted aminoalkylamides thereof, styrene, butadiene and isoprene. Preferred comonomers include styrene, acrylic acid, [2-hydroxy-3-(1-[4-methylpiperazinyl])-propyl] methacrylate and especially methyl methacrylate.

A wide variety of cross-linking monomers, which impart a 3-dimensional network character and water insolubility to the final polymer, can be used, for example, acrylic monomers or olefin compounds and others known in the art. Representative of such monomers are 1,3-butylene diacrylate, ethylene glycol dimethacrylate, 1,3-butylene dimethacrylate, 1,6-hexamethylene diacrylate, ethylene diacrylate, diethylene glycol dimethacrylate, N,N′-methylenebisacrylamide, neopentyl glycol dimethacrylate, 1,1,1-trimethylolethane trimethacrylate, divinylbenzene and the like. Preferred cross-linking monomer is N,N′-methylenebisacrylamide.

The polymerization and copolymerization reactions are initiated by free radicals. Suitable free-radical initiator systems are those which generate free radicals at a suitable rate for polymerization or copolymerization under the mild conditions necessitated by the thermal sensitivity of the cell enzyme moiety. Redox initiator systems are preferred for this reason. Representative of such systems are peroxy compounds such as ammonium, sodium, or potassium persulfate, benzoyl peroxide, and di(sec-butyl)peroxydicarbonate in combination with a reducing agent such as sodium thiosulfate, sodium metabisulfite, ferrous ammonium sulfate hexahydrate, dimethylaminopropionitrile or riboflavin. Preferred initiator system is dimethylaminopropionitrile - ammonium persulfate.

The polymer composition can vary considerably, with the preferred composition being, in terms of molar percent of total monomer, about 15 to 90 percent cell-reactive monomer, about 0 to 60 percent comonomer, and about 10 to 40 percent cross-linking monomer. These proportions are preferred whether the cells are bonded to monomer or to preformed polymer.

In certain cases, the cells are treated with a polyfunctional cross-linking reagent to reduce enzyme loss from the cells. While the exact mechanisms involved are not fully understood, it is believed that one class of the polyfunctional reagents reacts with, and thereby cross-links, amino groups of the cell membrane, thus effectively reducing the porosity of the membrane; the other class accomplishes this result by activating the carboxyl groups present in the membrane which then react with membrane amino groups through amide bond formation. Typical examples of the first class include such reagents as pyruvic aldehyde, glyoxal, hydroxyadipaldehyde, cyanuric chloride, tetraazotized o-dianisidine, bis-diazotized benzidine, 1,3-difluoro-4,6-dinitrobenzene, toluene 2,4-diisocynate, and especially glutaraldehyde, while the second class includes such reagents as ethyl chloroformate and water-soluble carbodiimides, for example, 1-ethyl-3-(3′-dimethylaminopropyl)carbodiimide hydrochloride.

The cells can be treated either before, during or after attachment to reactive monomer or polymer. As with the cell bonding, the treatment is run in aqueous medium. While the cells can be effectively treated over a wide temperature range, the preferred range is from about 5° to 50°C, and especially from about 10° to 30°C. Depending upon the temperature and agent employed, the treatment normally requires from about 0.5 to 10 hours, preferably from about 2 to 4 hours. The amount of agent required can vary considerably, usually from about 1 to 50 weight percent of the cells (dry basis), and preferably from about 5 to 25 weight percent.

The disclosed cell immobilization to water-insoluble polymer through chemical covalent bonding, with optional treatment to minimize enzyme leakage from the cells, yields a stable immobilized enzyme system without the need to isolate a desired enzyme. And because of its stability and readily filterable particulate form, the product can be effectively used in aqueous catalytic chemical processes requiring either recycle batch or continuous operation.

The following examples are merely illustrative and are not to be construed as limiting the invention, the scope of which is defined by the appended claims.

EXAMPLE 1

To 80 g glycidyl methacrylate plus 1.0 liter of water was added with stirring 30 g of N,N'-methylenebisacrylamide. After the mixture was stirred for 15 minutes at room temperature, 10 g of methyl methacrylate was added, the mixture was cooled to about 5°C and nitrogen gas was bubbled into the cold mixture for 15 minutes. Then 20 ml of dimethylaminopropionitrile and 2 g of ammonium persulfate were added. The mixture under nitrogen was stirred at 10°C until polymerization began, then an additional hour at ambient temperature, and finally left to stand for 2 hours. About 750 ml of water was added to the resulting solid, and the mixture was stirred vigorously to break up the polymer. The solids were filtered, washed with water and air dried to give 120 g of white particulate polymer.

An A. niger (NRRL-3; Pfizer Culture FD 2454) fermentation broth, grown under submerged aerobic conditions at 33°C and pH 5.8–7.0 on glucose substrate, was filtered and the cells were washed with water and expressed to a semi-dry paste. The cells (250 g, 55 g dry) were placed in a solution containing 22 g of 25 weight percent aqueous glutaraldehyde in 1000 ml of water. The suspension was adjusted to pH 6.2 and stirred for 1 ¾ hours at room temperature. The solids were filtered and washed with water to give 104 g of wet treated cells possessing 76% of the original glucose oxidase activity.

A suspension of 32 g of wet treated cells and 16 g of the glycidyl methacrylate polymer in 240 ml of water was stirred for 30 hours at room temperature and the filtered. The solids were washed with water to give 126 g of wet immobilized cells having 58% of the glucose oxidase activity of the original untreated cells.

EXAMPLE 2

To a slurry of 600 mg of wet treated A. niger cells prepared as in Example 1 (23 units glucose oxidase activity/100 mg) in 20 ml of acetonitrile was added simultaneously 600 mg of methacryloyl chloride and 400 mg of triethylamine. The mixtue was stirred at room temperature for 2 hours, then placed in 20 ml of water (resulting pH 6.03). To the aqueous mixture under nitrogen was added 1.3 g of N,N'-methylenebisacrylamide, 750 mg of methyl methacrylate and 300 mg of acrylic acid. The mixture was adjusted to pH 6.7 and treated with 0.5 ml of dimethylaminopropionitrile and 250 mg of ammonium persulfate. After 2 hours the reaction was treated with an additional 150 mg of ammonium persulfate and was allowed to stir for another hour. An equal volume of water was added to the reaction and the mixture was centrifuged. The residue was filtered and washed with water to give 32.25 g of wet immobilized cells containing 78% of the glucose oxidase activity of the original untreated cells.

EXAMPLE 3

The wet immobilized cells of Example 1 (47.3 g) were placed in 100 ml of an aqueous solution containing 10 g of glucose, and the mixture was stirred with aeration for 21 hours at room temperature. A 99% conversion to a mixture of gluconic acid and delta gluconolactone was obtained, and 75% of the original enzyme activity was recovered.

This oxidation can be repeated using 30 g of the wet immobilized cells of Example 2 in 20 ml of an aqueous solution containing 2 g of glucose, with comparable conversion and enzyme activity recovery.

EXAMPLE 4

A *Proteus rettgeri* (ATCC 9250; Pfizer Culture FD 18470-76-60) fermentation broth, grown under submerged aerobic conditions at 28°C and pH 6.8-7.0 on lactic casein substrate, was centrifuged and the cells were repulped in water and expressed to a semi-dry paste. To a slurry of the wet cells (7.5 g dry weight) in 100 ml of water was added 4 g of 25 weight percent aqueous glutaraldehyde. The mixture was stirred at about pH 7.0 for 3 hours and was then centrifuged. The treated cells were resuspended in 100 ml of water, and 7.5 g of the glycidyl methacrylate polymer of Example 1 was added with stirring. The mixture was stirred at about pH 7.0 and room temperature for about 30 hours. The solids were filtered, washed with water and stored as a wet cake until used. The immobilized cells contained 65% of the activity of the original untreated cells as measured by the rate of conversion of penicillin G to 6-aminopenicillanic acid.

EXAMPLE 5

To a slurry of 20 g (5.0 g dry) of the immobilized *Proteus rettgeri* cells of Example 4 in 500 ml water at pH 8.0 and 37°C was added 5 g of potassium penicillin G. The pH of the slurry was maintained at 8.0 by the monitored addition of 1N NaOH, and the hydrolysis was complete after about 3 hours. The immobilized cells were filtered, washed with water and stored as a wet cake for further use. The filtrate was adjusted to pH 2 with 2N HCl and extracted with ethyl acetate. The resulting aqueous layer was adjusted to pH 4.3 with 2N NaOH, concentrated and cooled to give a white crystalline solid. The crystals were filtered, washed with water and air dried to give 2.17 g (75% yield) of pure 6-aminopencillanic acid. The immobilized cells still retained about 50% of the penicillin acylase activity of the original immobilized cells of Example 4 after 20 hydrolysis cycles.

EXAMPLE 6

To a stirred mixture under nitrogen of 3.6 g of bromoacetylhydroxyethyl methacrylate in 15 ml of water was added 375 mg of N,N'-methylenebisacrylamide. The mixture was cooled to 5°C and treated with 0.25 ml of dimethylaminopropionitrile and 38 mg of ammonium persulfate. The mixture was stirred slowly at room temperature until polymerization began. The stirrer was then stopped and the reaction mixture was allowed to stand at room temperature for 2 hours. The resulting slurry was diluted with 25 ml of water and filtered. The cake was washed with water and air dried to give 3.7 g of particulate polymer.

Wet expressed *Proteus rettgeri* cells grown and isolated as in Example 4 (10 g, 2 g dry) were placed in a solution containing 0.8 g of 25 weight percent aqueous glutaraldehyde in 50 ml water. The suspension was adjusted to pH 7.0, stirred for 3 hours at room temperature and centrifuged. The treated cells were repulped in 50 ml water and expressed to a semi-dry paste.

A suspension of 10 g of the treated cells and 20 g of the bromoacetylhydroxyethyl methacrylate polymer in 120 ml water was stirred for 30 hours at room temperature and pH 7.0. The mixture was filtered and the cake was washed with water to give 36.8 g of wet immobilized cells having 75% of the penicillin acylase activity of the original untreated cells.

EXAMPLE 7

To a slurry of 46 g of the wet immobilized cells of Example 6 in 500 ml water at pH 8.0 and 37°C is added 5 g of potassium penicillin G. The pH of the slurry is maintained at 8.0 by the monitored addition of 1N NaOH, and the hydrolysis is complete after about 3 hours. The immobilized cells are filtered, washed with water and stored as a wet cake until further use. The filtrate is adjusted to pH 2 with 2N HCl and extracted with ethyl acetate. The resulting aqueous layer is adjusted to pH 4.3 with 2N NaOH, concentrated and cooled to give crystalline 6-amino-penicillanic acid.

EXAMPLE 8

A suspension of 25 g of wet treated *A. niger* cells as in Example 1 and 2 g of glycidyl methacrylate in 60 ml of water was stirred for 17 hours at 7°C. The suspension was then added to a mixture of 2.2 g of N,N'-methylenebisacrylamide, 2 ml of styrene, 450 mg of methyl methacrylate, 0.5 ml of dimethylaminopropionitrile and 1.5 g of [2-hydroxy-3-(1-[4-methylpiperazinyl])propyl] methacrylate in 40 ml of water at pH 6.8. The mixture, under nitrogen, was treated with 200 mg of ammonium persulfate and stirred for 3 hours at room temperature. The reaction solids were filtered and washed with water to give 43.6 grams of wet immobilized cells having 75% of the glucose oxidase activity of the original untreated cells.

EXAMPLE 9

The wet immobilized cells (28.3 g) of Example 8 were placed in 200 ml of an aqueous solution containing 20 g of glucose, and the mixture was stirred with aeration for 21 hours at room temperature. An 80% yield of a mixture of gluconic acid and delta gluconolactone was obtained. The reaction slurry was filtered and the solids were washed with water to give 28 g of wet immobilized cells having 82% of the original enzyme activity.

EXAMPLE 10

A suspension of 5 g of wet expressed *Proteus rettgeri* cells, grown and isolated as in Example 4, and 10 g of glycidyl methacrylate polymer of Example 1 in 65 ml of water was stirred for 24 hours at room temperature. The mixture was filtered and the filter cake was washed with water to give 26.9 g of wet immobilized cells having 62% of the initial penicillin acylase activity.

The immobilized cells (25 g, 1 g dry cell weight) were placed in a solution containing 0.4 g of 25 weight percent aqueous glutaraldehyde in 50 ml of water. The suspension was adjusted to pH 7.0 and stirred for 3 hours at room temperature. The slurry was filtered and the filter cake was washed with water to give 23.2 g of wet treated immobilized cells having 79% of the penicillin acylase activity of the untreated immobilized cells.

EXAMPLE 11

To a slurry of 12 g of the wet treated immobilized cell preparation of Example 10 in 100 ml of water at pH 8.0 and 37°C is added 1 g of potassium penicillin G. The pH of the reaction is maintained at 8.0 by the monitored addition of 1N NaOH and the reaction is complete after about 3 hours. The immobilized cell material is filtered, washed with water and stored as a wet cake until further use. The filtrate is adjusted to pH 2 with 2N HCl and extracted with ethyl acetate. The resulting aqueous layer is adjusted to pH 4.3 with 2N NaOH, concentrated and cooled to give crystalline 6-APA.

EXAMPLE 12

A suspension of *A. niger* cells grown and isolated as in Example 1 (20 g, 4 g dry) and 8 g of glycidyl methacrylate in 100 ml water was adjusted to pH 7.5 and shaken at room temperature for 18 hours. N,N'-methylenebisacrylamide (1.5 g) was added and the resulting slurry was stirred under nitrogen for 15 minutes, then cooled to 5°C, treated with 150 mg of ammonium persulfate plus 1 ml of dimethylaminopropionitrile, and stirred at ambient temperature for 3 hours. The reaction solids were filtered and washed with water to give 71 g of wet immobilized cells having 62% of the original glucose oxidase activity.

The immobilized cells (18 g, 1 g dry cell weight) were placed in a solution containing 0.4 g of 25 weight percent aqueous glutaraldehyde in 100 ml water. The suspension was adjusted to pH 7.0 and stirred for 3 hours at room temperature. The solids were filtered and washed with water to give 17.3 g of wet treated immobilized cells having 75% of the glucose oxidase activity present in the immobilized cells before glutaraldehyde treatment.

EXAMPLE 13

The wet treated immobilized cells (14 g) of Example 12 are placed in 15 ml of an aqueous solution containing 1.5 g of glucose, and the mixture is stirred with aeration for about 21 hours at room temperature, with conversion to gluconic acid and recovery of enzyme activity comparable to those of Example 3.

EXAMPLE 14

*Rhodotorula gracilis* cells (NRRL Y 1091; Pfizer Culture FD 6521) were isolated from a fermentation broth, grown under submerged aerobic conditions at 28°C and pH 6.8–7.0 on glucose substrate, by centrifugation. Fifty grams of washed cells in 250 ml of water were treated with 5 g of glycidyl methacrylate polymer of Example 1. The mixture was stirred at room temperature for about 20 hours. The suspension was filtered and the filter cake was washed with water to give 63 g of wet immobilized cells containing 49% of the original phenylalanine ammonia-lyase activity.

EXAMPLE 15

A suspension of 14.74 g of wet immobilized cells of Example 14 in 30 ml of water containing 2.25 g of trans-cinnamic acid, 652 mg of ammonium chloride and 3.3 ml of concentrated ammonium hydroxide was adjusted to pH 9.5. The mixture was shaken at 37°C for 18 hours giving about 90% yield of L-phenylalanine, based on recovered cinnamic acid. The reaction solids were filtered and washed with water to give 14 g of wet immobilized cells containing 77% of their original phenylalanine ammonia-lyase activity. The L-phenylalanine was isolated from the filtrate using standard procedures.

EXAMPLE 16

A suspension of 40 g of washed *Rhodotorula gracilis* cells, grown and isolated as in Example 14, plus 8 g of glycidyl methacrylate in 80 ml of water was adjusted to pH 7.2 and stirred at room temperature for 1.5 hours. N,N'-methylenebisacrylamide (1.5 g) was added and the resulting slurry was stirred under nitrogen for 10 minutes, then cooled to 5°C, treated with 150 mg of ammonium persulfate plus 1 ml of dimethylaminopropionitrile, and stirred at room temperature for three hours. The final reaction slurry was diluted with water and filtered. The polymer cake was washed with water to give 62.3 g of wet immobilized cells having 44% of the original phenylalanine ammonia-lyase activity.

EXAMPLE 17

A suspension of 15 g of wet immobilized cells of Example 16 in 30 ml of water containing 1.12 g of trans-cinnamic acid, 320 mg of ammonium chloride and 1.6 ml of concentrated ammonium hydroxide is adjusted to pH 9.5. The mixture is shaken at 37°C for about 18 hours with L-phenylalanine formation comparable to that of Example 15.

EXAMPLE 18

A suspension of 15 g of wet expressed *Proteus rettgeri* cells, grown and isolated as in Example 4, and 30 g of glycidyl methacrylate polymer of Example 1 in 100 ml of water was stirred at room temperature and pH 7 for 18 hours. The suspension was then centrifuged and the solids were washed with water to give 100 g of wet immobilized cells containing 100% of the original penicillin acylase activity.

To a slurry of 25 g of the wet immobilized cells in 70 ml of water at pH 8.0 and 37°C was added 1 g of potassium penicillin G. The hydrolysis, maintained at pH 8.0 by the monitored addition of 1N NaOH, was complete in about 3 hours. The slurry was then filtered, and the immobilized cells were washed with water and stored as a wet cake for further use. The effectiveness of these cells for the production of 6-aminopenicillanic acid was not as great as with the immobilized cells of Example 4, however, since the cells retained only 15% of the penicillin acylase activity of the original cells after only 2 hydrolysis cycles.

EXAMPLE 19

To 25 g of 2-hydroxyethyl methacrylate in 100 ml of water was added 12.5 g of cyanogen bromide dissolved in 100 ml of water. The mixture was immediately adjusted to pH 11 with 5N NaOH, causing the reaction temperature to rise to 46°C, and then maintained at that pH until no further base was required. The mixture was then cooled to room temperature, adjusted to pH 6.5 and treated with a slurry of 50 g of freeze-dried *Proteus rettgeri* cells, previously grown and isolated as in Example 4 before drying, in 500 ml of water. The resulting suspension was stirred for 45 minutes. Then 25 g of acrylamide and 2.5 g of N,N'-methylenebisacrylamide were added, and the suspension was stirred for 15 minutes, cooled to 4°C and treated with 4 ml of dimethylaminopropionitrile plus 425 mg of ammonium persulfate. The polymerization mixture was allowed to warm to room temperature and stand 1 hour. The mixture was then blended, using a Waring blender, and centrifuged. The gel-like centrifuge solids were resuspended in water, recentrifuged, washed with water and freeze-dried to give 112 g of dry immobilized cells containing 19% of the original penicillin acylase activity.

EXAMPLE 20

To a suspension of 20 g of wet expressed *Proteus rettgeri* cells, grown and isolated as in Example 4, in 80 ml of water was added 1 g of 25 weight percent aqueous glutaraldehyde and 10 g of glycidyl methacrylate. The suspension was adjusted to pH 6.8 and stirred at room temperature for 2 hours. The mixture, under nitrogen, was then treated with 1.9 g of N,N'-methylene-bisacrylamide and 2 ml of dimethylaminopropionitrile, adjusted to pH 7 and treated with 200 mg of ammonium persulfate. The resulting suspension was stirred for ½ hour and then allowed to stand at room temperature for 1 ½ hours. The solids were filtered and washed with water to give 81.3 g of wet immobilized cells containing 54% of the original penicillin acylase activity of the untreated cells.

The wet immobilized cells are useful in the conversion of potassium penicillin G to 6-aminopenicillanic acid as described in Example 7 with comparable results.

EXAMPLE 21

A *Bacterium cadaveris* (ATCC 9760; Pfizer Culture FD 24016) fermentation broth, grown under submerged aerobic conditions at 28°C and pH 6-8 on protein hydrolysate substrate, is centrifuged and the cells are repulped in water and expressed to a semi-dry paste. To a slurry of the wet cells (7.5 g dry weight) in 100 ml of water is added 4 g of 25 weight percent aqueous glutaraldehyde. The mixture is stirred for about 2 hours at pH 7 and then centrifuged. The treated cells are resuspended in 100 ml of water and 7.5 g of glycidyl methacrylate polymer of Example 1 is added with stirring. The mixture is stirred at about pH 7.0 and room temperature for about 30 hours. The solids are filtered, washed with water and stored as a wet cake until used.

EXAMPLE 22

Fumaric Acid (120 g) is added to 140 ml of concentrated ammonium hydroxide. The mixture is adjusted to pH 8.5 with ammonium hydroxide and the reaction volume is adjusted to 600 ml with water. Immobilized cells of Example 21 containing 7000 u of aspartate ammonia-lyase activity are added and the mixture is stirred at 37°C for about 4 hours. The reaction slurry is filtered and the filtrate is adjusted to pH 2.8 with sulfuric acid to precipitate aspartic acid.

What is claimed is:

1. A process for immobilizing microbial cells comprising contacting said cells with a polyfunctional cross-linking reagent, contacting the so-treated cells in aqueous medium with a water-insoluble particulate polymer and continuing said contacting until said cells are covalently bonded to said polymer, said polymer resulting from polymerization, in the presence of a cross-linking monomer and polymerization initiator, of a monomer of the formula:

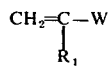

wherein
$R_1$ = hydrogen, methyl or chloro,
and

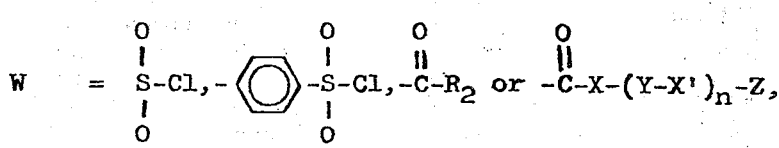

wherein
$R_2$ = halo, azido, 2,3-epoxypropoxy, 2,3-epithiopropoxy, N-(2,3-epoxypropyl)amino, N-[(p-diazonium chloride)phenyl]amino, acryloyloxy, lower alkoxy carbonyloxy, or benzenesulfonyloxy,
X = oxygen or $NR_3$ where $R_3$ is hydrogen or alkyl of from 1 to 6 carbons,
Y = alkylene containing 2 or 3 carbons,
n = an integer of from 1 to 2,
Z = haloacetyl, 2-(4,6-dichloro)-s-triazinyl, p-toluenesulfonyl, p-(halomethyl)benzoyl, or cyano, and
X' = X with the proviso that when Z is p-toluenesulfonyl, X' is oxygen.

2. The process of claim 1 wherein said polyfunctional cross-linking reagent is a reagent which cross-links amino groups of the membranes of said cells.

3. The process of claim 2 wherein said reagent is glutaraldehyde.

4. A composition containing immobilized microbial cells prepared by the process of claim 1.

5. The composition of claim 4 wherein $R_2$ is 2,3-eoxypropoxy.

6. The composition of claim 4 wherein Z is haloacetyl.

7. The composition of claim 4 wherein said cells contain the enzyme penicillin acylase.

8. The composition of claim 4 wherein said cells contain the enzyme glucose isomerase.

9. A process for immobilizing microbial cells comprising contacting said cells with a polyfunctional cross-linking reagent, contacting the so-treated cells in aqueous medium with a water-insoluble polymerizable ethylenically unsaturated monomer having amino-reacting groups, continuing said contacting until said cells are covalently bonded to said monomer and subsequently polymerizing said monomer in the presence of a cross-linking monomer and polymerization initiator, said ethylenically unsaturated monomer being of the formula:

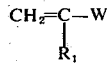

wherein
$R_1$ = hydrogen, methyl or chloro,
and

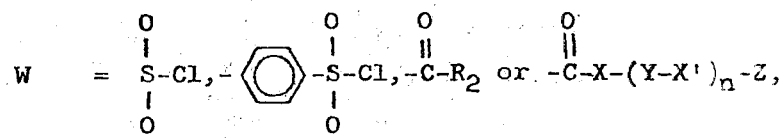

wherein
$R_2$ = halo, azido, 2,3-epoxypropoxy, 2,3-epithiopropoxy, N-(2,3-epoxypropyl)amino, N-[(p-diazonium chloride)phenyl]amino, acryloyloxy, lower alkoxy carbonyloxy, or benzenesulfonyloxy,
X = oxygen or $NR_3$ where $R_3$ is hydrogen or alkyl of from 1 to 6 carbons,
Y = alkylene containing 2 or 3 carbons,
n = an integer of from 1 to 2,
Z = haloacetyl, 2-(4,6-dichloro)-s-triazinyl, p-toluenesulfonyl, p-(halomethyl)benzoyl, or cyano, and
X' = X with the proviso that when Z is p-toluenesulfonyl, X' is oxygen.

10. The process of claim 9 wherein said polyfunctional cross-linking reagent is a reagent which cross-links amino groups of the membranes of said cells.

11. The process of claim 10 wherein said reagent is glutaraldehyde.

12. A composition containing immobilized microbial cells prepared by the process of claim 9.

13. The composition of claim 12 wherein $R_2$ is 2,3-epoxypropoxy.

14. The composition of claim 12 wherein Z is haloacetyl.

15. The composition of claim 12 wherein said cells contain the enzyme penicillin acylase.

16. The composition of claim 12 wherein said cells contain the enzyme glucose isomerase.

17. The composition of claim 12 wherein said cells contain the enzyme aspartate ammonia-lyase.

18. A process for immobilizing microbial cells comprising the steps of contacting said cells in aqueous medium with glutaraldehyde, subsequently contacting said cells in aqueous medium with glycidyl methacrylate monomer, continuing said contacting until said cells are covalently bonded to said monomer; and subsequently polymerizing said monomer in aqueous medium in the presence of N,N'-methylenebisacrylamide monomer and dimethylaminopropionitrile-ammonium persulfate.

* * * * *

UNITED STATES PATENT AND TRADEMARK OFFICE
CERTIFICATE OF CORRECTION

PATENT NO. : 3,957,580
DATED : May 18, 1976
INVENTOR(S) : Roger P. Nelson

It is certified that error appears in the above-identified patent and that said Letters Patent are hereby corrected as shown below:

Column 1 line 6 change "immobilied" to --immobilized--.

Column 4 line 60 change "2,4-diisocynate" to -- 2,4-diisocyanate --.

Column 5 line 39 "A. niger" should be italicized.

Column 5 line 53 change "the" to --then--.

Column 5 line 59 "A. niger" should be italicized.

Column 7 line 35 change "6-amino-penicillanic" to -- 6-aminopenicillanic --.

Column 7 line 38 "A. niger" should be italicized.

Column 11 line 56 (claim 5 line 1) change "2,3-eoxy-" to -- 2,3-epoxy- --.

Signed and Sealed this

Twenty-second Day of February 1977

[SEAL]

Attest:

RUTH C. MASON
*Attesting Officer*

C. MARSHALL DANN
*Commissioner of Patents and Trademarks*